(12) United States Patent
Hartwell

(10) Patent No.: US 8,785,059 B2
(45) Date of Patent: Jul. 22, 2014

(54) POWER GENERATION

(75) Inventor: Edward Yerbury Hartwell, York (GB)

(73) Assignee: Smith & Nephew PLC, London (GB)

( * ) Notice: Subject to any disclaimer, the term of this patent is extended or adjusted under 35 U.S.C. 154(b) by 604 days.

(21) Appl. No.: 13/119,164

(22) PCT Filed: Sep. 14, 2009

(86) PCT No.: PCT/GB2009/051182
§ 371 (c)(1),
(2), (4) Date: Mar. 15, 2011

(87) PCT Pub. No.: WO2010/032038
PCT Pub. Date: Mar. 25, 2010

(65) Prior Publication Data
US 2011/0171543 A1 Jul. 14, 2011

(30) Foreign Application Priority Data
Sep. 17, 2008 (GB) .................................. 0817041.7

(51) Int. Cl.
*H01M 8/16* (2006.01)
(52) U.S. Cl.
USPC ......................................................... 429/401
(58) Field of Classification Search
USPC ......................................................... 429/401
See application file for complete search history.

(56) References Cited

U.S. PATENT DOCUMENTS 6,294,281 B1 * 9/2001 Heller ........................... 429/401

FOREIGN PATENT DOCUMENTS

| EP | 1 541 191 A1 | 6/2005 |
| EP | 1541191 | * 6/2005 |
| GB | 2 307 180 A | 5/1997 |
| WO | WO 03/106966 A | 12/2003 |
| WO | WO 2004/037334 | 5/2004 |
| WO | WO 2005/046760 | 5/2005 |
| WO | WO 2005/105180 | 11/2005 |
| WO | WO 2006/072782 A | 7/2006 |

OTHER PUBLICATIONS

International Search Report for International Application No. PCT/GB2009/051182, mailed Mar. 12, 2010, in 6 pages.

* cited by examiner

*Primary Examiner* — Ula C Ruddock
*Assistant Examiner* — Jacob Marks
(74) *Attorney, Agent, or Firm* — Knobbe, Martens, Olson & Bear, LLP

(57) ABSTRACT

A method and apparatus are disclosed for generating electrical power during negative pressure therapy. The apparatus includes a fuel cell, comprising an anode element and a cathode element, arranged to collect biological fluid from a wound site to which a negative pressure is applied and electro-oxidize a component of the biological fluid at the anode element and/or electro-reduce a component of the biological fluid at the cathode element.

25 Claims, 3 Drawing Sheets

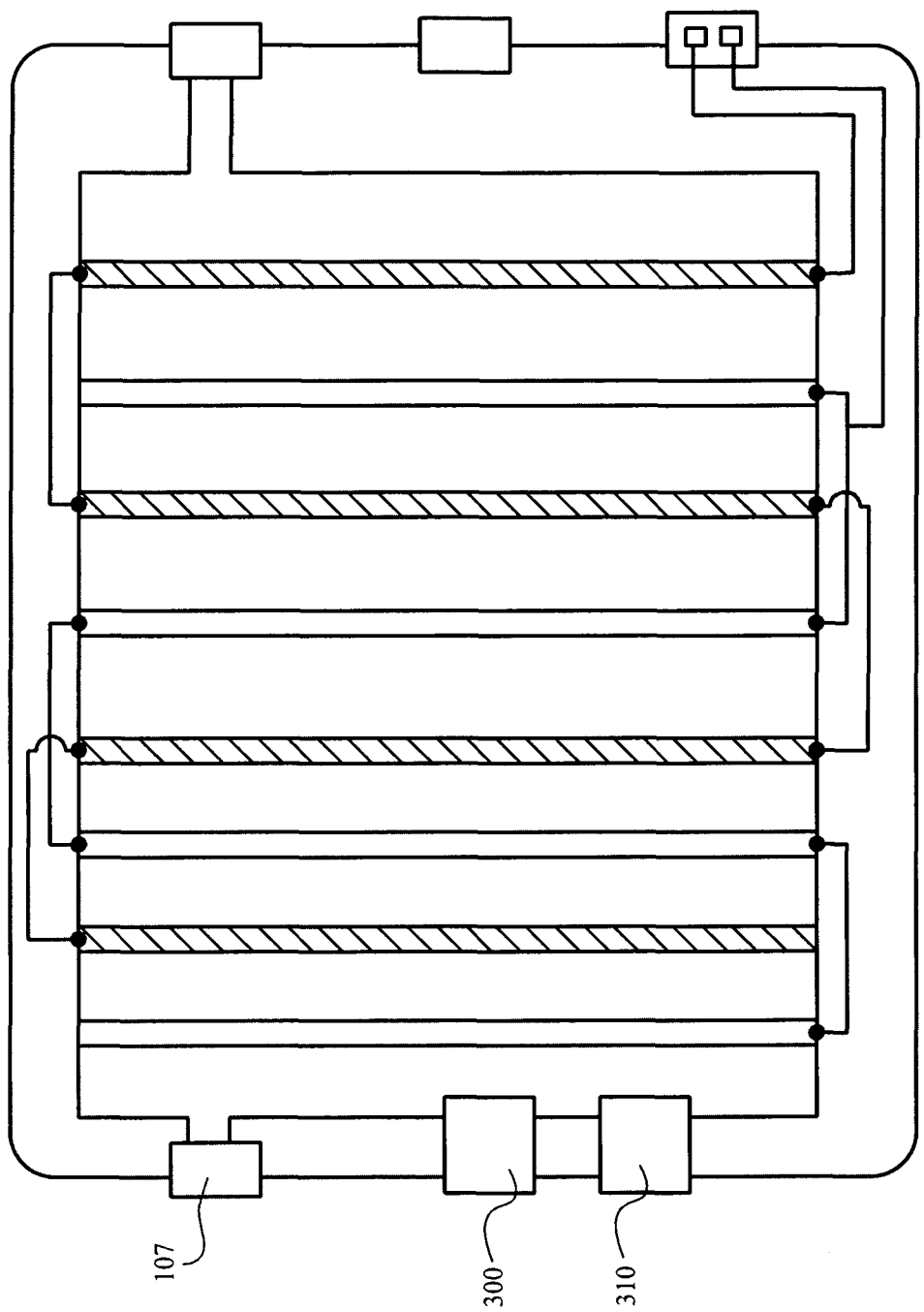

POWER GENERATION

CROSS-REFERENCE TO RELATED APPLICATIONS

This application is a U.S. National Phase of PCT International Application No. PCT/GB2009/051182, filed on Sep. 14, 2009, designating the United States and published on Mar. 25, 2010 as WO 2010/032038, which claims priority to Great Britain Patent Application No. 0817041.7, filed on Sep. 17, 2008. The disclosure of both prior applications is incorporated by reference in their entirety and should be considered a part of this specification.

BACKGROUND OF THE INVENTION

1. Field of the Invention

The present invention relates to a method and apparatus for providing electrical power when negative pressure is applied at a wound site. In particular, but not exclusively, the present invention relates to a method and apparatus for generating electrical power for a pump used to pump fluid from a cavity sealed over a wound site whereby power is generated using biological fluid collected from the wound site.

2. Description of the Related Art

There is much prior art available relating to the provision of apparatus and methods of use thereof for the application of topical negative pressure (TNP) therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In International patent application, WO 2004/037334, apparatus, a wound dressing and a method for aspirating, irrigating and cleansing wounds are described. In very general terms, the application describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above-noted references is included herein by reference.

However, the above described apparatus and methods are generally only applicable to a patient when hospitalised as the apparatus used is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus. To this end GB-A-2 307 180 describes a portable TNP therapy unit which may be carried by a patient and clipped to belt or harness. A negative pressure is applied at a wound site but that pressure is prone to fluctuation which may have a detrimental effect to healing.

In this and other portable devices which carry a suction pump, power is typically provided for the pump by a mains supply or by one or more batteries. When a mains supply is used the portability of the device is limited restricting movement of a patient. When one or more batteries are used a lifetime associated with the battery becomes a limitation on a length of time over which a topical negative pressure therapy unit can be used. Furthermore there is a concern on the mind of a user that a battery may be about to expire leaving therapy uncompleted. Still furthermore batteries are relatively heavy and costly which can inconvenience a user as well as a provider of the therapy units.

U.S. Pat. No. 6,294,281 discloses a fuel cell having an anode and a cathode which is capable of using compounds from biological systems as fuel for generating electrical power. However, the number of biological systems suggested is limited. Furthermore a pumping mechanism must be provided for pumping fluid of a biological system into the fuel cell.

SUMMARY OF SOME EXEMPLIFYING EMBODIMENTS

It is an aim of the present invention to at least partly mitigate the above-mentioned problems.

It is an aim of certain embodiments of the present invention to provide a method for providing negative pressure at a wound site to aid in wound closure and healing in which electrical power for a pump used to provide the negative pressure is generated by a bi-product of the therapy itself.

It is an aim of certain embodiments of the present invention to provide a method and apparatus for generating electrical power by applying a negative pressure at a wound site, collecting biological fluid from the wound site and generating power using components of the collected biological fluid.

According to a first aspect of the present invention there is provided apparatus for generating electrical power during negative pressure therapy, comprising:

a fuel cell, comprising an anode element and a cathode element, arranged to collect biological fluid from a wound site to which a negative pressure is applied and electro-oxidise a component of the biological fluid at the anode element and/or electro-reduce a component of the biological fluid at the cathode element.

According to a second aspect of the present invention there is provided a method of generating electrical power during negative pressure therapy, comprising the steps of:

applying a negative pressure at a wound site;

collecting biological fluid from the wound site in a fuel cell comprising an anode element and a cathode element; and electro-oxidising a component of the biological fluid at the anode element and/or electro-reducing a component of the biological fluid at the cathode element.

According to a third aspect of the present invention there is provided a method for providing negative pressure at a wound site, comprising the steps of:

providing a sealed cavity over a wound site;

via a pump member in fluid communication with the sealed cavity, pumping fluid from the cavity;

collecting biological fluid pumped from the wound site in a fuel cell comprising an anode element and a cathode element; and generating electrical power for the pump member by electro-oxidising a component of the biological fluid at the anode element and/or electro-reducing a component of the biological fluid at the cathode element.

Certain embodiments of the present invention provide the advantage that a bi-product of negative pressure therapy can itself be used to generate power usable either for a pump providing the negative pressure or for a variety of other electrical devices such as lights, sensors and/or displays etc.

Certain embodiments of the present invention provide the advantage that a waste canister of a therapy unit can be used as a fuel cell. This can be disposable and highly portable as well as being relatively lightweight. The dual purpose use also means parts for the apparatus used to provide negative therapy are reduced.

BRIEF DESCRIPTION OF THE DRAWINGS

Embodiments of the present invention will now be described hereinafter, by way of example only, with reference to the accompanying drawings in which:

FIG. 3 illustrates an alternative fuel cell.

DETAILED DESCRIPTION OF SOME EXEMPLIFYING EMBODIMENTS

Figure 1:
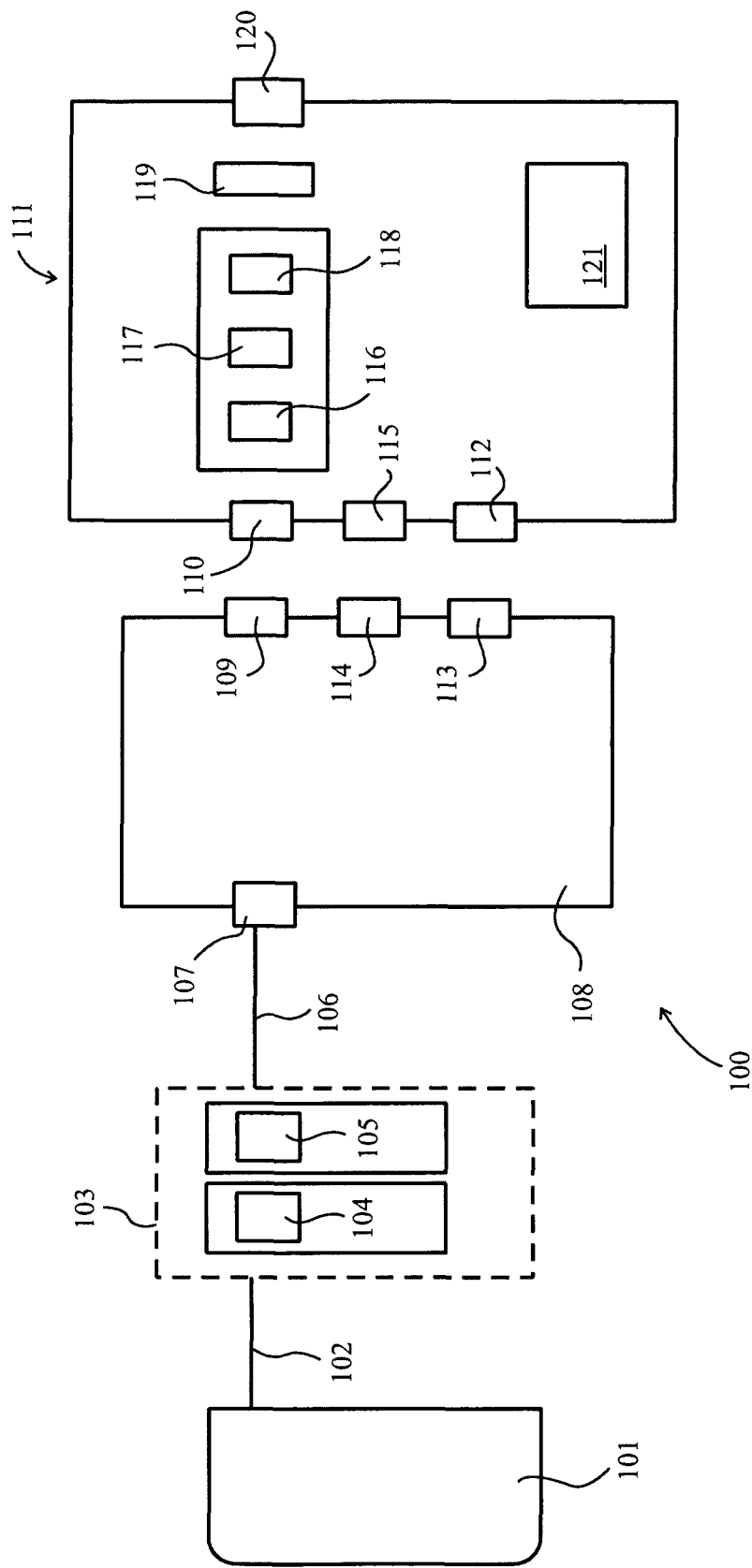
FIG. 1 illustrates a general view of an apparatus and the constituent apparatus features thereof.

FIG. 1 illustrates a generalised schematic view of an apparatus 100 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and reducing bacterial load (and thus infection risk). In addition, the therapy allows for less disturbance of a wound leading to more rapid healing.

As illustrated in FIG. 1 the apparatus 100 includes a dressing 101 which can be located over a wound site to be treated. The dressing 101 forms a sealed cavity over the wound site. A conduit 102 in fluid communication with the cavity connects the cavity to an inline connector 103 which includes first and second connectors 104, 105. A further conduit 106 connects the aspiration conduit 102 through the connectors to flow entry orifice 107 of a waste canister 108. A flow exit orifice is connected to a further fluid connector 109 is in fluid communication with a corresponding further fluid connector 110 which acts as an entry/suction port of a device unit 111. The device unit 111 and waste canister 108 are provided with mating connectors 112, 113 such as catches which secure the device unit 111 to the waste canister 108 in a releasably secure fashion. Other connecting mechanisms can of course be used.

The waste canister 108 also acts as a fuel cell, as will be described hereinbelow, which generates electrical power. Electrical connectors 114 from the waste canister thus mate with corresponding electrical connectors 115 of the device unit 111 so that the generated power can be used by electrical components in the device unit.

The device unit 111 includes an electrical pump 116 and optionally a pressure monitor 117 and flow meter 118. The aspiration path takes the aspirated fluid, which in the case of fluid on the exit side of the exit port 109 of the canister is gaseous, through a silencer system 119 and final filter 120. The final filter 120 has an activated charcoal matrix which ensures that no odours escape with the gas exhausted from the device unit 111.

The device unit 111 also includes a control system 121 which controls a user interface and power management system.

The overall apparatus can be used to provide TNP therapy to a patient in almost any environment. The apparatus is lightweight and does not need batteries or to be connected to the mains supply. It will be appreciated that batteries and/or mains connectors may optionally be utilised as a backup or primary power source.

It is to be noted that the dressing 101 may be any type of dressing normally employed with TNP therapy and in very general terms may comprise, for example, a semi-permeable flexible, self-adhesive drape material. Such dressings are well-known in the art. These cover a wound site and seal with surrounding sound tissue to create a sealed cavity or void over the wound.

The aspiration conduits 102, 106 may be plain flexible tubes, for example, having a single lumen therethrough and made from a plastics material compatible with raw tissue. Multi lumen conduits are, of course, optional.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

It will be appreciated that according to certain alternative embodiments of the present invention the canister 108 may be located downstream of the pump.

Figure 2:
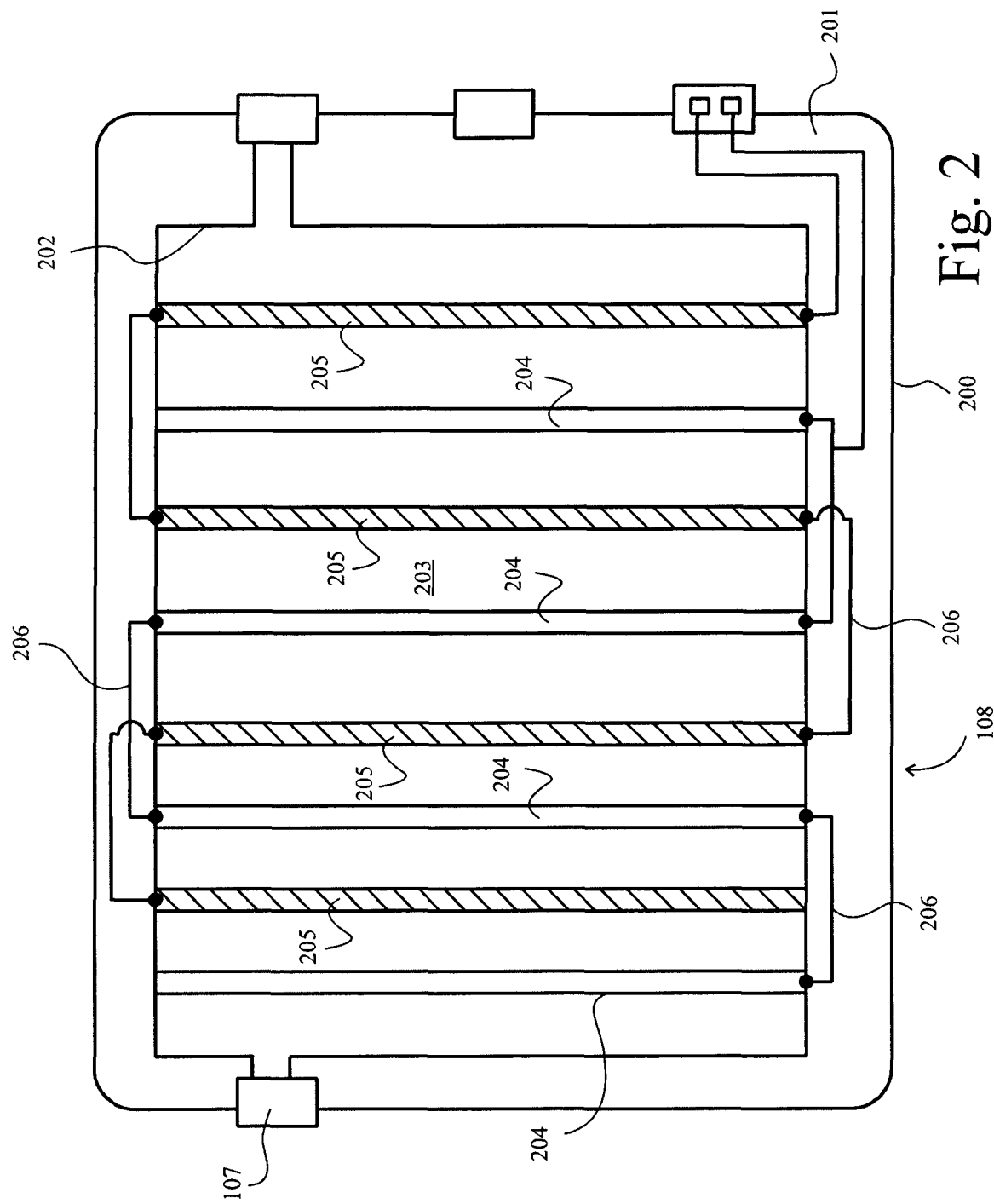
FIG. 2 illustrates a fuel cell.

FIG. 2 illustrates the waste canister 108 in more detail. The waste canister 108 includes an outer surface 200 of a housing 201. An inner surface 202 of the housing 201 defines an inner chamber 203. The waste canister 108 thus acts as the body of a fuel cell. Baffle plates 204, 205, extend across the chamber 203 to prevent fluid in the chamber, particularly liquid, from flowing around too readily when the waste canister is moved. Eight baffle plates are illustrated in FIG. 2 although it will be appreciated that different numbers of plates are possible according to further embodiments of the present invention. The baffle plates themselves are electrically coupled together via connectors 206. Through bores may optionally be formed to provide fluid communication to different zones within the chamber. Further baffle plates may be used which do not form part of an anode or cathode but which baffle fluid flow in the fuel cell. It will also be appreciated that the electrodes may be in other shapes than the plates such as rods etc.

The baffle plates are arranged in a substantially parallel spaced apart configuration and provide an anode and cathode for the fuel cell. As illustrated in FIG. 2 the multiple baffle plates 204, which are electrically coupled together, provide an anode whilst the further plurality of baffle plates 205, which are likewise electrically coupled together, provide a cathode. The anode and cathode of the present invention can be arranged as per the anode and cathode disclosed in U.S. Pat. No. 6,294,281 (which is incorporated herein by reference). To this end an anode electrolysis layer is formed on at least a portion of the anode. The anode electrolysis layer typically includes an anode redox polymer and an anode enzyme. Likewise, the cathode has a cathode electrolysis layer typically including a cathode redox polymer and a cathode enzyme formed on at least a portion of the cathode. More than one redox polymer and/or more than one enzyme can be used in each electrolysis layer. The electrolysis layers may be formed on all or less than all of the plates. In optional embodiments of the present invention the anode electrolysis layer and/or cathode electrolysis layer may be covered by a non-fouling coating. This coating prevents or retards the penetration of macro-molecules, such as proteins, having a molecular weight of 5000 daltons or more into the electrodes of the fuel cell. This can be accomplished using a polymeric film or coating having a pore size smaller than the biomolecules that are to be excluded or by having an ionic and/or cationic functional groups that repel cationic or anionic macro-molecules respectively.

The enzyme in each electrolysis layer typically catalyzes an electro-chemical reaction of a cathode oxidant or anode reductant. Usually the anode reductant is electro-oxidised at the anode and the cathode oxidant is electro-reduced at the cathode. The redox polymer transduces a current between the cathode oxidant or anode reductant and the respective electrode. In general the cathode oxidant and anode reductant are provided within a biological fluid extracted from the wound site which enters the chamber of the fuel cell via flow entry orifice 107. The cathode oxidant may be oxygen whilst the anode reductant may include sugars, alcohols and/or carboxylic acids. The biological fluid will, of course, include other components in addition to these which may be electro-oxidised or electro-reduced.

The redox polymers on the anode and/or cathode enable compounds to be electrolysed as redox polymers generally provide for adequate transport of electrons. Various types of redox polymer may be utilised as indicated in U.S. Pat. No. 6,294,281.

The enzymes of the anode and/or cathode electrolysis layers catalyse an electro-chemical reaction of an anode reductant or cathode oxidant respectively. Various types of enzymes are usable as indicated in U.S. Pat. No. 6,294,281.

At the anode plate one or more sugars, alcohols and/or carboxylic acids typically found in the biological fluid are electro-oxidised. Preferred anode enzymes for the electro-oxidisation of the anode reductant include, for example, PQQ glucose dehydrogenase, glucose oxidase, galactose oxidase, PQQ fructose dehydrogenase, quinohemoprotein alcohol dehydrogenase, pyranose oxidase, oligosaccharide dehydrogenase, and lactate oxidase.

In an embodiment of the fuel cell the cathode reduces gaseous oxygen that is typically dissolved in the biological fluid or originating from air. In another embodiment hydrogen peroxide is formed in a non-enzyme-catalysed electrode reaction or in an enzyme-catalyzed reaction on or off the cathode and then the hydrogen peroxide is electro-reduced at the cathode. Preferred cathode enzymes for the reduction of $O_2$ and $H_2O_2$ include, for example, tyrosinase, horseradish peroxidise, soybean peroxidise, other peroxidises, laccases, and/or cytochrome C peroxidises.

As negative pressure is applied to the wound site, biological fluid which is extracted is continuously input into the chamber of the fuel cell through the flow inlet 107. Gaseous fluid is extracted through the fluid exit orifice 109 via one or more filters. Thus for continuously producing power the reactant-carrying biological fluid typically flows through the fuel cell constantly replenishing the anode reductant and/or cathode oxidant exhausted by reacting at the anode and/or cathode respectively. Furthermore, as fluid levels in the fuel cell rise new regions of the baffle plates making up the anode and cathode are revealed and thus are continuously provided.

It will be appreciated that degassing of the electrodes is advantageously improved by the partial vacuum in the canister. Bubble movement may also facilitate agitation and flow of fluid between electrodes. Positioning of the fluid inlet around a bottom of the canister will aid this.

Alternatively or additionally a fixed bleed can be included in the canister to increase the air agitation. Optionally further agitation may be added via addition of an impeller in the canister.

The electrical power generated by the fuel cell is provided to a pump in the device unit 111 by the electrical terminals in the connector 113. It will be appreciated that according to further embodiments of the present invention the electrical power generated by the fuel cell may be used to operate a variety of devices in addition to, or as an alternative to, the pump of the negative pressure therapy unit.

It will be appreciated that prior to power generation a fluid containing electro-oxidisable and/or electro-reducable components must first be introduced in the fuel cell. This will be utilised to power a pump, if necessary because there is no alternative power source, until wound exudate from a wound site begins to be introduced through the flow inlet. To this end the fuel cell may be preloaded with a desired quantity of fluid.

FIG. 3 illustrates an alternative embodiment of the present invention in which a fluid inlet orifice 300 and fluid outlet valve 310 are provided. The fluid inlet orifice can be opened prior to pumping of the unit to receive a fluid useable as a power source for the fuel cells. For example, a glucose solution may be injected through the fluid inlet orifice 300. The fuel cell/waste canister may be disposable or alternatively may include the outlet valve 310 for draining depleted biological fluid as the fluid level in the fuel cell grows. In this way biological fluid in which a concentration of the required electro-reducable or electro-oxidisable components have fallen below a predetermined threshold may be exhausted. The valve 310 may then subsequently be closed and new biological fluid introduced via the flow inlet 107.

According to certain embodiments of the present invention biological fluids from a patient are collected in the waste canister of a negative pressure wound therapy device. These fluids, particularly wound exudate containing anode reductants, such as glucose, sugars, carbohydrates, carboxylic acids, alcohols and cathode oxidants, such as oxygen, can be made to flow through a fuel cell in the canister via pre-filtration of particulates and pathogens. The flow of such biological fluids replenishes a source of electro-oxidants and electro-reductants in the fuel cell thus enabling the constant production of electrical energy. A bi-product of the therapy can thus be used to provide electrical power for the therapy itself.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. Apparatus for generating electrical power during negative pressure therapy, comprising:
    a dressing configured to seal a wound site;
    a fuel cell, comprising:
        an anode element and a cathode element, arranged to collect biological fluid from the wound site to which a negative pressure is applied and electro-oxidize a component of the biological fluid at the anode element and/or electro-reduce a component of the biological fluid at the cathode element;
    at least one conduit configured to connect the wound site to a flow entry orifice of the fuel cell;
    a negative pressure source configured to be connected to the fuel cell and configured to generate negative pressure at the wound site; and
    a waste canister, wherein the waste canister comprises the fuel cell.

2. The apparatus as claimed in claim 1, wherein the biological fluid comprises wound exudate and/or oxygen.

3. The apparatus as claimed in claim 1, wherein the fuel cell further comprises a plurality of baffle plates each comprising a respective portion of the anode element and/or cathode element.

4. The apparatus as claimed in claim 3, further comprising at least one through passageway provided in each baffle plate.

5. The apparatus as claimed in claim 1, wherein the fuel cell further comprises a pathogen filter at a flow exit orifice of the fuel cell.

6. The apparatus as claimed in claim 1, wherein the fuel cell further comprises a filter at a flow entry orifice of the fuel cell.

7. The apparatus as claimed in claim 1, wherein the fuel cell further comprises first and second electrical connectors, each connected to at least a respective one of the anode element or cathode element.

8. The apparatus as claimed in claim 1, wherein the fuel cell further comprises a fluid inlet orifice for receiving a glucose solution prior to application of a negative pressure at the wound site.

9. The apparatus as claimed in claim 1, wherein the fuel cell further comprises a fluid outlet valve for emptying the fuel cell subsequent to a concentration of said components in the biological fluid dropping below a predetermined level.

10. The apparatus as claimed in claim 1, wherein the apparatus is battery-less.

11. The apparatus as claimed in claim 1, wherein the apparatus is portable.

12. The apparatus as claimed in claim 1, wherein the fuel cell is disposable.

13. The apparatus as claimed in claim 1, further comprising an anode enzyme and/or an anode redox polymer disposed on the anode and/or a cathode enzyme and/or a cathode redox polymer disposed on the cathode.

14. A method of generating electrical power during negative pressure therapy, comprising:
    applying a negative pressure from a negative pressure source to a dressing sealing a wound site;
    collecting biological fluid from the wound site in a waste canister, the waste canister comprising a fuel cell comprising an anode element and a cathode element; and
    electro-oxidizing a component of the biological fluid at the anode element and/or electro-reducing a component of the biological fluid at the cathode element,
    wherein the negative pressure source is connected to the fuel cell, and
    wherein the wound site is connected via at least one conduit to a flow entry orifice of the fuel cell.

15. The method as claimed in claim 14, further comprising:
    electro-oxidizing an anode reductant component of the biological fluid on the anode element in the presence of an anode enzyme and/or electro-reducing a cathode oxidant component of the biological fluid on the cathode in the presence of a cathode enzyme.

16. The method as claimed in claim 14, further comprising:
    collecting the biological fluid comprising wound exudate in the waste canister.

17. The method as claimed in claim 14, further comprising:
    preventing undesired flow of fluid collected in the fuel cell via a plurality of baffle plates each comprising respective portions of the anode element and/or cathode element, located within a chamber region of the fuel cell.

18. The method as claimed in claim 14, further comprising:
    replenishing biological fluid in the fuel cell by pumping wound exudate from the wound site to the fuel cell via a pump powered by electrical power generated by the fuel cell.

19. The method as claimed in claim 14, further comprising:
    prior to collecting biological fluid from the wound site, providing a quantity of glucose solution to the fuel cell; and
    generating electrical power by electro-oxidizing and/or electro-reducing a component of the glucose solution.

20. The method as claimed in claim 14, further comprising powering at least one electrical device.

21. A method for providing negative pressure at a wound site, comprising:
    pumping fluid from the cavity a wound site sealed by a dressing via a pump member in fluid communication with the dressing;
    collecting biological fluid pumped from the wound site in a waste canister, the waste canister comprising a fuel cell comprising an anode element and a cathode element; and
    generating electrical power for the pump member by electro-oxidizing a component of the biological fluid at the anode element and/or electro-reducing a component of the biological fluid at the cathode element,
    wherein the pump member is connected to the fuel cell, and
    wherein the wound site is connected via at least one conduit to a flow entry orifice of the fuel cell.

22. The method as claimed in claim 21, further comprising:
    electro-oxidizing an anode reductant component of the biological fluid on the anode element in the presence of an anode enzyme and/or electro-reducing a cathode oxidant component of the biological fluid on the cathode in the presence of a cathode enzyme.

23. The method as claimed in claim 21, further comprising: collecting the biological fluid comprising wound exudate in the waste canister.

24. The method as claimed in claim 21, further comprising: preventing undesired flow of fluid collected in the fuel cell via a plurality of baffle plates each comprising respective portions of the anode element and/or cathode element, located within a chamber region of the fuel cell.

25. The method as claimed in claim 21, further comprising: prior to collecting biological fluid from the wound site, providing a quantity of glucose solution to the fuel cell and generating electrical power by electro-oxidizing and/or electro-reducing a component of the glucose solution.

* * * * *

UNITED STATES PATENT AND TRADEMARK OFFICE
CERTIFICATE OF CORRECTION

| | | |
|---|---|---|
| PATENT NO. | : 8,785,059 B2 | Page 1 of 1 |
| APPLICATION NO. | : 13/119164 | |
| DATED | : July 22, 2014 | |
| INVENTOR(S) | : Edward Yerbury Hartwell | |

It is certified that error appears in the above-identified patent and that said Letters Patent is hereby corrected as shown below:

In the Claims:

In column 8 at line 50, In Claim 21, change "from the cavity" to --from--.

Signed and Sealed this
Seventeenth Day of March, 2015

Michelle K. Lee
*Director of the United States Patent and Trademark Office*